US009612168B2

(12) United States Patent
Garden et al.

(10) Patent No.: US 9,612,168 B2
(45) Date of Patent: Apr. 4, 2017

(54) SENSOR FOR DIFFERENTIAL CALORIMETRIC MEASUREMENT, AND METHOD FOR MANUFACTURING SAME

(75) Inventors: Jean-Luc Garden, Echirolles (FR); Gael Moiroux, Grenoble (FR); Pierre Lachkar, Grenoble (FR)

(73) Assignees: CENTRE NATIONAL DE LA RECHERCHE SCIENTIFIQUE, Paris (FR); SETARAM INSTRUMENTATION, Caluire (FR)

( * ) Notice: Subject to any disclaimer, the term of this patent is extended or adjusted under 35 U.S.C. 154(b) by 448 days.

(21) Appl. No.: 14/128,413

(22) PCT Filed: Jun. 18, 2012

(86) PCT No.: PCT/IB2012/053057
§ 371 (c)(1),
(2), (4) Date: Dec. 20, 2013

(87) PCT Pub. No.: WO2012/176107
PCT Pub. Date: Dec. 27, 2012

(65) Prior Publication Data
US 2014/0140365 A1  May 22, 2014

(30) Foreign Application Priority Data
Jun. 21, 2011  (FR) ...................... 11 55432

(51) Int. Cl.
*G01K 17/00* (2006.01)
*G01N 25/48* (2006.01)
(Continued)

(52) U.S. Cl.
CPC ............ *G01K 17/00* (2013.01); *C23F 1/00* (2013.01); *C23F 4/00* (2013.01); *G01K 17/006* (2013.01); *G01N 25/482* (2013.01)

(58) Field of Classification Search
CPC .................................................. G01K 17/006
(Continued)

(56) References Cited

U.S. PATENT DOCUMENTS

| 6,193,413 | B1* | 2/2001 | Lieberman | ........... | G01K 17/006 |
| | | | | | 374/43 |
| 9,176,012 | B2* | 11/2015 | Lieberman | ........... | G01K 17/006 |
| 2005/0242341 | A1* | 11/2005 | Knudson | ................ | H05K 3/007 |
| | | | | | 257/40 |

OTHER PUBLICATIONS

Zuo et al ("Design and Fabrication of Differential Scanning Nanocalorimeter for Biological Applications", Proceedings of the ASME 2011 International Design Engineering Technical Conferences & Computers and Information in Engineering Conference IDETC/CIE, Aug. 28-31, 2011, pp. 1-9).*

(Continued)

*Primary Examiner* — Minh Phan
*Assistant Examiner* — Leon W Rhodes, Jr.
(74) *Attorney, Agent, or Firm* — Oblon, McClelland, Maier & Neustadt, L.L.P.

(57) ABSTRACT

A sensor for differential calorimetric measurement including a thermometric cell and another cell, each cell including: a membrane of a low thermal conductivity material, having first and second surfaces; and a mechanism supporting the membrane, of a high thermal diffusivity coefficient material, in contact with the first surface of the membrane, the thermometric cell including at least two active thermometric elements located on the first surface of the membrane, the two cells configured to be assembled such that the second surfaces of the membranes of the cells are opposite one another, a sample and a reference used for taking measurement configured to be placed between the two membranes and directly in contact with the second surfaces, and at least one of the cells including a sealing mechanism opposite the first surface of the membrane, wherein a free space for a gas is arranged between the sealing mechanism and the membrane.

14 Claims, 3 Drawing Sheets

Figure 1:
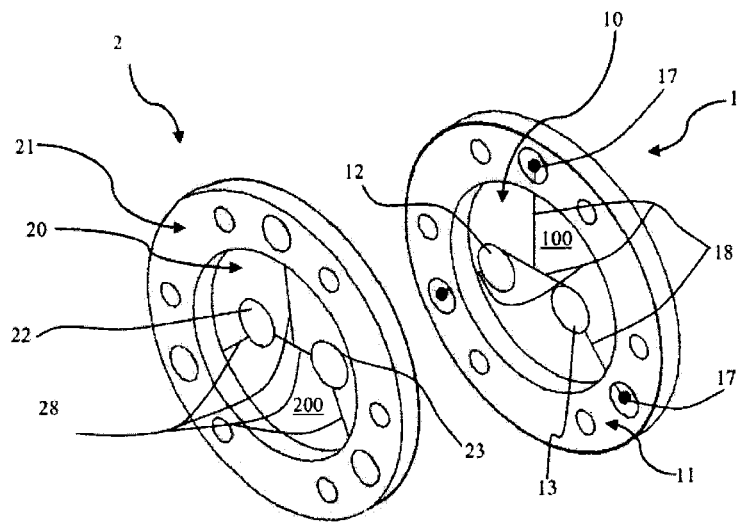

(51) Int. Cl.
*C23F 1/00* (2006.01)
*C23F 4/00* (2006.01)

(58) Field of Classification Search
USPC .......................................................... 374/12
See application file for complete search history.

(56) References Cited

OTHER PUBLICATIONS

International Search Report issued Sep. 10, 2012 in PCT/IB2012/053057.

J.L. Garden, et al., "Thermodynamics of small systems by nanocalorimetry: From physical to biological nano-objects" Thermochimica Acta, vol. 492, No. 1-2, XP026305549, Aug. 10, 2009, pp. 16-28.

E. Zhuravlev, et al., "Fast scanning power compensated differential scanning nano-calorimeter: 2. Heat capacity analysis" Thermochimica Acta, vol. 505, No. 1-2, XP027053546, Jun. 10, 2010, pp. 14-21.

V.H. Carreto-Vasquez, et al., "Miniaturized calorimeter for thermal screening of energetic materials" Microelectronics Journal, vol. 41, No. 12, XP027504857, Dec. 1, 2010, pp. 874-881.

J.L. Garden, et al., "Non-equilibrium heat capacity of polytetrafluoroethylene at room temperature" Thermochimica Acta, vol. 461, No. 1-2, XP022184815, Aug. 6, 2007, pp. 122-136.

\* cited by examiner

SENSOR FOR DIFFERENTIAL CALORIMETRIC MEASUREMENT, AND METHOD FOR MANUFACTURING SAME

The invention relates to the field of calorimetry and, more particularly, a differential calorimetric measurement sensor and its manufacturing method.

Numerous calorimeters are already known, all of which are designed to measure the heat quantities involved in a chemical reaction or a substance transformation.

In practice, for example during a physical transformation, such as a phase transition, a heat exchange occurs between the substance and the outside environment, the direction of which depends on the endothermic or exothermic nature of the process of the transition.

Consequently, the measurement of the heat quantities makes it possible to access information on the structural state of the substance. This is why the calorimeters are used in many scientific fields, in particular physics and chemistry, and therefore in industry.

Industries notably affected are metallurgy, for the study of oxidoreduction reactions and thermal transitions, the chemistry of polymers or even biochemistry and the agro-food industry.

In particular, in biophysics, calorimetry is the only method that allows direct access to thermodynamic data (thermodynamic stability, free energy, entropy, etc.).

The known calorimeters implement different methods, notably differential scanning calorimetry, adiabatic calorimetry, isothermal calorimetry or even alternating current calorimetry or AC calorimetry.

The underlying basic principles of these methods are identical (presence of thermometric elements, sometimes one or more heating elements, one or more isothermal zones in very good thermal contact with the sample or the reference). However, each method has its own constraints, and an instrument or a sensor dedicated to one measurement method can be difficult to use for another.

For example, to increase the sensitivity of a sensor, the latter can be designed to operate in adiabatic conditions. Adiabicity (R) describes the degree of thermal insulation of the isothermal zone containing the sample in relation to the outside considered as a thermal bath.

If $R \gg 1$, then the calorimetric measurement is carried out in adiabatic conditions, and if $R \gg 1$, that is not the case.

Adiabicity is a relative criterion which depends on the dynamics of the calorimetric measurement method used. The criterion of adiabicity is defined by the value taken by the following ratio: $R=\tau/\Delta t_{mes}$, with $\tau=C/K$ which is the thermal time constant of the calorimeter. C is the heat capacity of the sample (and that of the sensor and that of the isothermal zone) and K is the heat exchange coefficient, or thermal conductance, sometimes called "heat leakage", which defines the thermal link between the sample and the thermal bath. $\Delta t_{mes}$ is the experimental timescale. It is the characteristic timescale on which the calorimetric measurement is carried out. It depends on the calorimetric method used.

In the case of AC calorimetry, the concept of adiabicity is defined relative to the temperature oscillation frequency. In this case, $\Delta t_{mes}=1/\omega$, where $\omega=2\pi f$ is the angular frequency of the temperature oscillation.

Reference is notably made to this method in the paper by Garden et al. "Thermodynamics of small systems by nanocalorimetry: from physical to biological nano-objects" Thermochimica Acta, vol. 492, Aug. 10, 2009, pages 16-28.

This paper describes a measurement sensor for an AC calorimetry method comprising a thermometric cell and a heating cell, intended to be assembled together, the thermometric cell comprising a membrane supporting an active element. This sensor is intended for small samples.

In this sensor, the heat leakage is established through the membrane. The measurement will be able to be carried out in adiabatic conditions by choosing a high temperature oscillation frequency, such that, even for a relatively low $\tau$ (small C), it will be possible to have $R=\omega\tau \gg 1$.

The present patent application focuses on DSC calorimetry (DSC standing for Differential Scanning calorimetry), which has been used to design the sensor according to the invention.

This analysis technique consists in measuring the differences of the heat exchanges between a sample to be analyzed and a reference, each being placed in a measurement cell.

As yet, the known measurement cells in the case of DSC calorimetry are not designed to operate in adiabatic conditions.

A differential measurement presents the advantage of eliminating most of the thermal drifts due to the environment, without adding noise to the system. Thus, it makes it possible to detect only the signal induced by the thermodynamic transformation to be studied.

Generally, when a calorimetric measurement sensor exists, regardless of the method used, and differential mode operation is desired, two sensors are manufactured that are as identical as possible with respect to their thermal properties. These two sensors are then mounted in a common thermal environment and the differential measurement is obtained from the results originating from the two independent sensors.

In practice, in this case, the two sensors retain the same thermal conditions, namely the same thermal insulation and the same thermal symmetry, for the active element present in the sensor.

By way of example, in the field of natural sciences, to study the thermodynamic trend of a protein, two identical cells are produced, these cells being connected to the environment in a thermally equivalent manner. One of them is filled with a volume of buffer solution, constituting the reference, the other being filled with a solution comprising the buffer solution and the protein, constituting the sample.

In practice, the two cells are placed in an oven whose temperature changes in a determined manner, generally according to ramps. This will lead to a physical transformation of the sample and therefore a heat flux exchanged between the sample and the oven. A differential measurement between the two measurement cells makes it possible to determine the heat flux difference between the sample and the reference and therefore directly obtain the useful signal generated by the protein.

Numerous appliances use the differential scanning calorimetry technique which includes a calibration prior to the measurement and a cleansing with an inert gas to avoid any reaction of the sample with the atmosphere of the oven.

These appliances have given satisfaction for a long time because they make it possible not only to measure the quantity of heat absorbed or released during a phase transition but also to observe more complicated phase changes, such as glass transitions.

Calorimeters that can notably be cited include those marketed by the companies Setaram, Mettler Toledo, Netzsch, TA Instruments and MicroCal for the largest, with only DSC calorimeters dedicated to the natural sciences from TA Instruments, MicroCal or Setaram.

The latter do, however, present drawbacks which relate notably to the minimum volume of the sample, necessary to perform a measurement. In practice, although the volume in the measurement zone is only a few hundred microliters, the minimum volume is of the order of a milliliter, to take account both of the volume of the measurement cell and of the minimum volume necessary to bring the product into the cell.

This minimum volume has proved prohibitive in the field of the natural sciences or in the pharmaceutical field, in which the samples to be studied are available in very small quantities, notably because of the cost of their synthesis. Furthermore, it is preferable for the concentration of sample molecules to be relatively low, so as to limit the problems of biochemical interaction and of aggregation.

Lastly, with the known calorimeters, the speed of the temperature ramps provided in the oven is limited to 2° C./min, because excessively high ramps would lead to temperature gradients in the sample, and therefore to unreliable measurements. This constitutes an obstacle for observing certain kinetic events induced by fast speeds, such as the glass transitions.

The company Mettler Toledo has recently marketed a calorimeter of DSC type that can work with tiny quantities of samples and scan speeds ranging up to $10^5$ Ks, but these instruments are only suited to measurements on solid samples.

The documents EP-1 351 052 and U.S. Pat. No. 6,079,873 describe calorimetric devices obtained by micro- and nano-fabrication techniques which are suited to calorimetric measurements on samples of small volume.

However, no industrial production of these devices is available.

Moreover, the device described in the document EP-1 351 052 does not make it possible to implement a differential scanning calorimetric analysis. This is because it is dedicated to the calorimetric detection of biochemical or biological interactions produced at constant temperature.

The device described in the document U.S. Pat. No. 6,079,873 comprises two suspended platforms, made of silicon, which serve as a support for the sample and the reference.

This device is limited in its applications because it does not allow for biological samples to be measured in aqueous solution. In practice, it is not designed to receive a liquid sample. It would be necessary for the latter to have only a very small volume. However, in this case, the sample would evaporate very quickly while generating stray thermal effects due to the evaporation. Lastly, the sample and reference are placed on the platforms. This results in very weak thermal couplings that provoke temperature gradients that disrupt the measurement for high temperature ramps, because the heat does not then have the time to be propagated throughout the sample.

The object of the invention is to mitigate these drawbacks by proposing an efficient differential calorimetric measurement sensor, designed for very small solid or liquid sample volumes and operating with much higher temperature ramps than the calorimeters available today on the market, while offering a resolution of the same order and being simple to manufacture.

Thus, the invention relates to a differential calorimetric measurement sensor comprising two cells, a thermometric cell and another cell, each cell comprising:
 a membrane made of a material with low thermal conductivity, with a first face and a second face, and
 support means for the membrane, made of a material exhibiting a high thermal diffusivity coefficient, typically greater than or equal to 1 $cm^2$/s, in contact with said first face of the membrane,
the thermometric cell comprising at least two active thermometric elements situated on said first face of the membrane, and the two cells being intended to be assembled in such a way that the second faces of the membranes of said cells are facing one another, a sample and a reference used to perform the measurement being able to be placed between the two membranes and directly in contact with said second faces and at least one of the cell comprising a closure means facing the first face of the membrane, a free space being formed between said closure means and the membrane for a gas.

Thus, the active elements are never in direct contact with a sample used to perform the measurement.

Moreover, all the active elements are produced on the same membrane, which simplifies the manufacturing method.

In a preferred embodiment, the other cell is a heating cell, at least two active heating elements being situated on said first face of the membrane of this other cell, such that each of said active heating elements is substantially aligned with one of said active thermometric elements of the thermometric cell, when the two cells are assembled together, a sample and a reference used to perform the measurement then being able to be placed between two active elements of each of the two cells.

In this case, a sample that is the object of the measurement is placed in direct contact with the second faces of the membranes between an active heating element of the heating cell and an active thermometric element of the facing thermometric cell, whereas a reference is placed between the other active heating element of the heating cell and the other active thermometric element of the thermometric cell.

Generally, the measurement sensor according to the invention is intended to be placed in an oven which makes it possible to regulate the temperature inside of the sensor and, optionally, apply temperature ramps.

When the sensor comprises a heating cell, the oven can be used to heat the sample placed inside the sensor to a constant temperature. The heating cell then makes it possible to apply temperature ramps almost instantaneously to the sample.

Advantageously, the second face of the membrane of at least one cell comprises, facing said at least two active elements, a layer made of a material exhibiting a high thermal conductivity, typically greater than 1 watt per centimeter and per kelvin (W/cm·K).

This layer is notably produced in gold and makes it possible to make the temperature of each active thermometric element uniform.

Advantageously, said support means are situated at the periphery of the membrane.

This arrangement makes it possible to thermally insulate the active elements of each cell in relation to said support means, by means of the membrane.

Preferably, the active elements of each cell are coated in a layer of electrically insulating material.

The presence of this layer also ensures a mechanical protection of the active elements of the cell.

Thus, with the measurement sensor according to the invention, the active thermometric and heating elements are situated on the same side as the membrane support means, which increases their mechanical strength.

The invention relates to a differential calorimeter comprising a measurement sensor according to the invention, an oven in which said sensor is arranged, and a cooling means.

This calorimeter advantageously comprises pressurized gas supply means which are in fluidic communication with the free spaces formed in the measurement sensor.

The invention also relates to a method for manufacturing a measurement sensor according to the invention consisting in producing two cells, a thermometric cell and another cell, the thermometric cell comprising a membrane made of a material with low thermal conductivity, this method comprising a step ($a_1$) during which at least two active elements are produced simultaneously on a first face of the membrane, and a step ($a_2$) in which support means exhibiting a high thermal diffusivity coefficient are fixed onto the first face of the membrane, the other cell being obtained by performing the preceding step ($a_2$), and the cells being intended to be assembled together, such that the second faces of the respective membranes of said cells are facing one another.

Preferably, prior to the step ($a_1$), a step ($a_0$) is performed in which the membrane is fixed onto a ring made of ceramic material, this ring being in contact with the second face of the membrane, the method consisting in carrying out the step ($a_2$) after the step ($a_1$), then a step ($a_3$) in which the ring is removed.

In a preferred embodiment of the method, the other cell is a heating cell which is obtained by implementing the preceding steps ($a_1$) and ($a_2$), at least two active heating elements being produced during the step ($a_1$), and possibly the steps ($a_0$) and ($a_3$).

The method according to the invention advantageously comprises a complementary step consisting in depositing, after the step ($a_1$), a layer of electrically insulating resin, so as to coat the active elements of at least one of the two cells.

Moreover, the method advantageously comprises another complementary step, after the step ($a_1$), consisting in depositing, on the second face of a membrane of at least one of the two cells, and facing an active element of said cell, a layer made of a material exhibiting a high thermal conductivity.

For the production of the thermometric cell, the step ($a_1$) preferably comprises the following steps:

($b_1$) a step of deposition of a layer of metal,
($b_2$) a lithography step, and
($b_3$) an ionic etching step.

Preferably, the metal deposited in the step ($b_1$) exhibits a high temperature coefficient, typically greater than $2.10^{-3}$ $K^{-1}$.

For the production of a heating cell, the step ($a_1$) preferably comprises the following steps:

($b'_1$) a step of deposition of a layer of metal,
($b'_2$) a lithography step, and
($b'_3$) a wet etching step.

Figure 2:
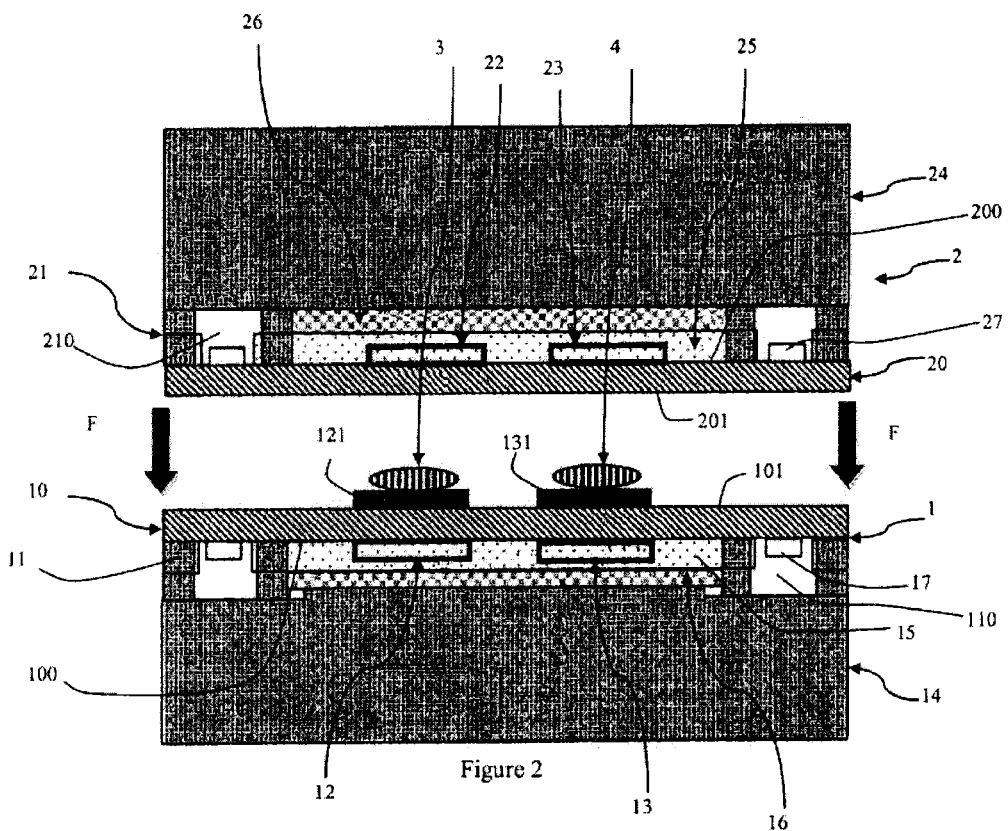

The invention will be better understood and other aims, advantages and features thereof will become more clearly apparent on reading the following description, which is given in light of the appended drawings, in which:

FIG. 1 is a perspective view schematically representing the two cells of an exemplary measurement sensor according to the invention, FIG. 2 is a cross-sectional view of the two cells of a measurement sensor according to the invention, and FIGS. 3 to 6 schematically represent the steps of production of a cell of a sensor according to the invention. The elements common to the different figures will be designated by the same references.

FIG. 1 shows, schematically and in perspective, a thermometric cell 1 and a heating cell 2.

Each of these cells comprises a membrane 10, 20.

This membrane is supported by means 11, 21. In the example illustrated, these support means take the form of a ring positioned at the periphery of the membrane 10, 20.

In practice, the ring 11, 21 is fixed onto a first face 100, 200 of the membrane.

On this same first face, the membrane 10, 20 comprises two active elements: the thermometric elements 12 and 13 and the heating elements 22 and 23.

The invention is not limited to the embodiment illustrated and the support means could take another form. However, the annular form illustrated in FIG. 1 makes it possible to obtain a thermal symmetry. In any case, the form retained should make it possible to thermally insulate the active elements from the support means. Moreover, the active thermometric elements should be thermally insulated from one another, like the heating elements.

As will emerge from the subsequent description of the production method, the active thermometric elements and the active heating elements are metallic resistors lithographed in thin layers, which allow for a very fast thermal response.

All these elements are produced simultaneously by the same manufacturing steps, which simplifies the manufacturing of the sensor.

This is made easy by the microfabrication techniques which are used to produce the cells and which will be described hereinbelow in the description. A sensor according to the invention with a considerable number of active elements would allow for calorimetric measurements in parallel on a large number of samples. This is interesting in the field of biology, in particular in the field of the design of medicines.

Placing two active elements on one and the same membrane does a priori present drawbacks.

As will be seen hereinbelow in the description, the possible thermal problems posed by the presence of a plurality of active elements on one and the same membrane are sorted out by virtue of a specific operation of the sensor.

The references 18 and 28 designate contact wires, making it possible to link the active elements of each cell to the contacts (not illustrated in FIG. 1).

Other features of the sensor according to the invention will now be described with reference to FIG. 2.

This FIGURE illustrates the two cells 1 and 2 of the sensor in their respective positions, prior to their assembly, the assembly being done according to the arrows F.

Compared to FIG. 1, the thermometric cell 1 has been flipped, so that it is the second faces 101 and 201 of the membranes 10 and 20 which are directly facing one another.

Moreover, on the support means 11, 21 of each cell, closure means 14, 24 (not illustrated in FIG. 1) are arranged.

FIG. 2 shows a preferred embodiment of the sensor according to the invention, in which the active elements 12, 13 and 22, 23 of each cell 1, 2 are coated in a layer of resin 15, 25. This layer of resin is not illustrated in FIG. 1.

FIG. 2 shows that the dimensions of the closure means 14, 24 and of the layer of resin 15, 25 are chosen such that a free space 16, 26 is formed between the layer of resin 15, 25 and the closure means 14, 24. The benefit of this space will be explained hereinafter in the description.

Lastly, the references 17, 27 designate the contacts to which the wires 18, 28 are linked. They can be accessed through throughholes 110, 210 formed in the support means 11, 21.

The membranes 10, 20 are produced in a material with low thermal conductivity, less than 10 mW/cm·K.

They can be typically produced in Kapton®, marketed by the company DuPont. This material exhibits a thermal conductivity $\lambda$ of 1.2 mW/cm·K and a specific heat of 1.13 J/gK.

Kapton® offers the advantage of being stable over a wide temperature range (from −269° C. to 400° C.) and of exhibiting a high chemical inertia.

Another polyimide can be used, such as that marketed under the name Upilex® by the company Ube Industries, which exhibits a thermal conductivity of 3 mW/cm·K.

This membrane has a micrometric thickness, typically between 10 and 100 μm. In this range of values, the membrane is sufficiently resistant, while still having low conductivity and exhibiting a heat capacity suited to the measurement of samples of small volume.

Thus, the membrane makes it possible to ensure a good thermal insulation while exhibiting a sufficient mechanical strength.

The membrane could also be made of glass, its thermal conductivity would then be approximately 10 mW/cm·K.

Moreover, the support means 11, 21 are made of a material exhibiting a high thermal diffusivity coefficient, typically greater than 1 W/cm·K.

The material which will preferably be used is copper, because it exhibits a very good thermal conductivity (approximately 4 W/cm·K) while having a reasonable manufacturing cost.

The closure means 14, 24 can also be made of copper.

Moreover, the closure means 14, 24 each include a piercing which is not illustrated in FIG. 2, this piercing being in communication with each of the spaces 16, 26.

These piercings will make it possible, using the sensor according to the invention, to inject a gas, notably nitrogen, at atmospheric pressure, into the spaces 16 and 26.

The presence of this pressurized gas will exert a force on the faces of the membranes with which it is in contact, which will ensure a good thermal contact between the two membranes 10 and 20, the latter sandwiching the sample or the reference, when the two cells are assembled together.

This will make it possible to better enclose the sample and the reference arranged between the two membranes.

In the example illustrated in FIG. 2, the height of the two closure means 14 and 24 is different. In practice, the height of the closure means 14 of the thermometric cell is adapted in such a way as to create a thermal conduction of predetermined value via the gas between the membrane 10 and the closure means 14. This is what will determine the thermal time constant of the measurement. The height of the closure means 24 of the heating cell 2 is adapted in such a way as to create a thermal conduction of negligible value via the gas between the membrane 20 and the closure means 24.

In practice, the closure means 24 could be omitted in as much as the pressure of the gas situated on the side of the second face 200 does not prevent a good contact being made between the two membranes.

Furthermore, in the example described, the thermometric cell comprises a closure means 14 by virtue of which the heat leakage is established by the gas present in the space 16.

However, the heating cell 2 could also be designed to fulfill this function by virtue of the closure means 24 and the space 26.

Similarly, the two cells could be designed symmetrically, the heat leakage then being equivalent on each cell.

The closure means 14, 24 illustrated in FIG. 2 could be omitted. In this case, the heat of the oven would be directly transmitted to the sample and to the reference placed between the two membranes of the sensor, through the membranes.

When at least one of the two is present, the thermal conduction between the external environment, typically an oven, on the one hand, and the sample and the reference, on the other hand, is obtained via at least one of these means and the gas present in one of the spaces 16, 26 and not through the membranes. This results from the fact that the thermal conductance through the gas is much greater than that through the membrane made of a material with low thermal conductivity.

It can also be noted that, by virtue of the closure means and the gas, the time constant of the sensor can be adjusted by modifying the pressure of the gas or the volume of the spaces 16, 26, that is to say the distance between the closure means and the membrane 10, 20. It can also be adjusted by appropriately selecting the nature of the gas, each gas having a different thermal conductivity.

This makes it possible to operate the sensor in adiabatic conditions, as a function of the value of the temperature ramp.

Thus, the pressurized gas has two functions: on the one hand, to enclose the sample and the reference between the two membranes and therefore ensure a significant thermal coupling and, on the other hand, to facilitate the conduction of the heat from the environment outside the sensor to the sample and the reference. The thermal conduction is obtained through the gas, even if the latter is not pressurized. The conduction would no longer occur anymore as in the case of secondary vacuum, with pressures of the order of $10^{-5}$ or $10^{-6}$ mbar.

Thus, with the sensor according to the invention, the thermal link between the sample and the thermal bath is produced via the gas situated behind the membrane. This distinguishes this sensor from the known sensors operating according to an AC calorimetry method. In practice, when these sensors include a membrane supporting an active element, the thermal link between the sample and the thermal bath is established through this membrane.

By virtue of the operation of the sensor, the possible thermal problems linked to the presence of a plurality of active elements on one and the same membrane no longer arise. In practice, the membrane no longer plays any role in establishing the thermal link between, on the one hand, the sample and the reference, and, on the other hand, the outside of the sensor.

In addition, with the sensor according to the invention, the temperature gradients in the sample and the reference are avoided. On the contrary, when the temperature gradients are established through a membrane, the latter imposes them on the sample and the reference.

FIG. 2 illustrates, facing each of the active elements 12 and 13 of the thermometric cell, a layer 121 and 131. This layer is made of a material exhibiting a high thermal conductivity, typically greater than 1 W/cm·K.

The material used is typically gold.

These two layers 121 and 131 are situated on the face 101 of the membrane 10, or on the face opposite the face 100 which receives the active elements 12 and 13.

However, the invention is not limited to this embodiment and these layers made of a material with high thermal conductivity could also be provided on the face 201 of the membrane 20, facing the active elements 22 and 23. Such layers could also be provided on the two faces 101, 201 of the membranes 10 and 20.

The sensor according to the invention is used as follows: A sample 3 is placed on the element 121 of the thermometric cell 1, whereas a reference 4 is placed on the element 131 of the cell 1.

The two cells are then assembled together by moving, for example, the cell 2 according to the arrows F and then by fixing them together when the membrane 20 comes into contact with the elements 121 and 131.

Thus, the sample and the reference are in contact with the second faces 101 and 201 of the membranes 10 and 20. On the other hand, the active elements of each cell are never in contact with the sample or the reference, since they are separated from them by a membrane 10, 20. The latter protects them from any contact with a liquid (or a solid), despite its small thickness.

Moreover, the membrane 10, 20 thermally insulates the sample or the reference from the support means 11, 21 and also the sample from the reference, which contributes to increasing the resolution of the sensor. On the other hand, a thermometric element 12, 13 is in good thermal contact with the corresponding heating element 22, 23. In as much as the constituent material of the membranes exhibits a low thermal conductivity, there is no need to structure them to make them more insulating and their mechanical strength is reinforced. The thickness of the membranes is thus greater than that of the platforms described in the document U.S. Pat. No. 6,079,873.

In FIGS. 1 and 2, a sensor is shown comprising a thermometric cell 1 and a heating cell 2. However, the sensor could operate without the cell 2 including any active heating elements. In this case, the heating of the sample and of the reference, if provided, will be ensured by the oven in which the sensor is intended to be placed. When the heating is ensured by the oven alone, the temperature of the sample and of the reference follows the temperature ramp applied by the oven with a certain delay. However, when the heating is ensured both by the oven and by the heating cell, the temperature of the sample and of the reference follows the temperature ramp applied by the oven almost instantaneously. This makes it possible to apply much faster temperature ramps.

The steps of production of a thermometric cell of a sensor according to the invention will now be described with reference to FIGS. 3 to 6. They correspond to a preferred embodiment of the method for manufacturing a sensor according to the invention.

Figure 3:
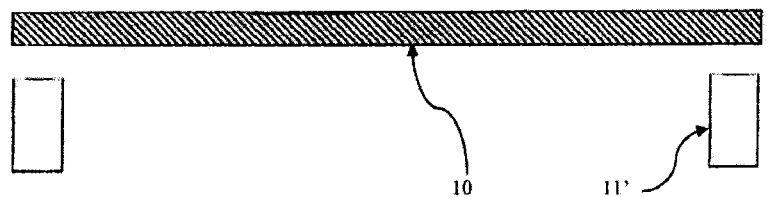

FIG. 3 illustrates the membrane 10 of the thermometric cell.

In practice, this membrane is obtained by being punched out from a polyimide sheet, notably a sheet of Kapton®.

As illustrated in FIG. 1, this membrane 10 is circular. Any other form could be chosen, the circular form having the advantage of thermal symmetry.

The reference 11' designates a ring made of a ceramic material. More generally, the ring can be made of any machinable material exhibiting a very low thermal expansion coefficient, typically less than $10^{-5}/°C$.

This ring can notably be made of Macor® which is a ceramic marketed by the company Corning Incorporated.

This material can be used at high temperature. It exhibits an average thermal conductivity ($\lambda$=1.46 W/m/°C.) and a low thermal diffusivity ($a=7.3.10^{-7}$ m$^2$/s). It also exhibits a low thermal expansion coefficient ($114.10^{-7}$/°C. from 20 to 600°C.) which enables it to remain rigid and not to be deformed at high temperature. Finally, it exhibits a high chemical inertia. It therefore does not interfere with the microfabrication steps which are implemented, notably to produce the active elements of the cells.

The membrane 10 is intended to be bonded to the ring made of ceramic 11'.

Figure 4:
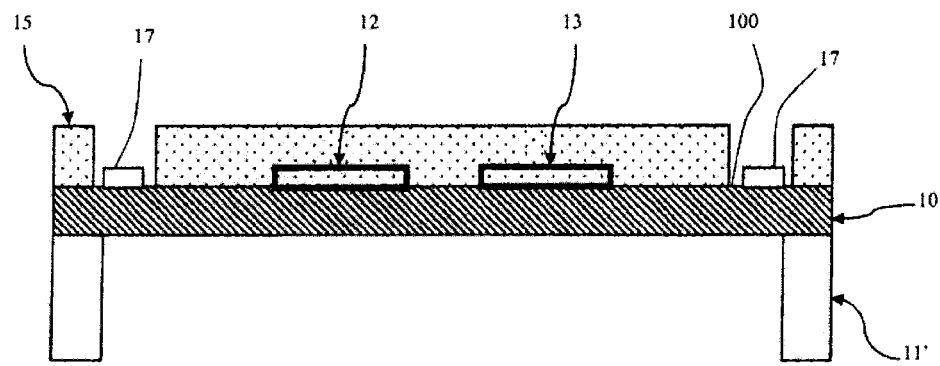

On the first face 100 of the membrane 10, the active elements 12 and 13 of the thermometric cell, illustrated in FIG. 4, are then produced.

These active elements are obtained by virtue of the following steps which use microelectronics techniques.

A layer of metal will first of all be deposited on the membrane 10.

As an example, the material used is platinum which is deposited by magnetron sputtering.

Other materials could be used. Generally, a chemically stable metal exhibiting a high temperature coefficient is suitable for this application.

Preferably, a so-called bond coat is deposited on the membrane 10, before the deposition of the platinum. This bond coat can notably consist of a tungsten and titanium alloy. Chromium is also perfectly suitable.

The thickness of the layer of platinum is typically 0.36 μm, whereas that of the bond coat is typically 0.01 μm.

The platinum in a thin layer exhibits a fairly high temperature coefficient ($\alpha$=2 to $3.10^{-3}K^{-1}$), which gives it a great thermal sensitivity. This is why this metal is very commonly used in the fabrication of thermometers. Furthermore, its high chemical inertia gives it a stability in time that is very great even at high temperatures, which is not the case with thermocouples in general.

The next step is a lithography step which makes it possible to obtain the desired pattern on the layer of platinum. This pattern is protected by the deposition of a layer of resin, which is then hardened.

The last step is an ionic etching step, by virtue of which the metallic layer is eliminated from the surface of the membrane, in areas not covered by the pattern.

Thus, the method according to the invention makes it possible to produce the active elements by implementing one and the same step of thin layer deposition, one and the same microphotolithography step and one and the same etching step. They are therefore produced simultaneously.

The production method is therefore considerably simplified, compared to a method consisting in producing two independent sensors each comprising an active element.

Furthermore, since the active elements are obtained simultaneously by the same manufacturing steps, they therefore exhibit almost identical electrical characteristics. This identity is essential in a differential measurement.

Preferably, the thermometric elements 12 and 13 take the form of a disc and are situated in the central part of the membrane 10.

The form of a disc is preferred because it ensures a thermal symmetry. However, other forms could be envisaged. Moreover, by being situated in the central part of the membrane, the elements 12 and 13 are insulated substantially identically relative to the ring 11.

The thermometric elements obtained exhibit a very low heat capacity, which is 0.652 mJ/K.

During this lithography step, the contacts 17 and the contact wires 18 are also produced. A soldering step is subsequently applied to ensure the electrical contact between the wires and the contacts.

The two thermometric elements can be mounted according to a Wheatstone bridge type scheme to directly obtain the differential temperature between the sample and the reference.

The next step of the method consists in depositing a layer of resin on all of the first face 100 of the membrane 10, apart from the zones of the membrane supporting the contacts 17.

This layer of resin 15 makes it possible to electrically insulate the thermometric elements 12 and 13 and ensure a mechanical protection.

This resin can notably be a photosensitive polyimide which is hardened after a bake step. As an example, the polyimide PoliFuji 2210 A®, marketed by the company Fujifilm, can be cited.

On completion of the steps which have just been described, the product illustrated in FIG. 4 is obtained.

Figure 5:
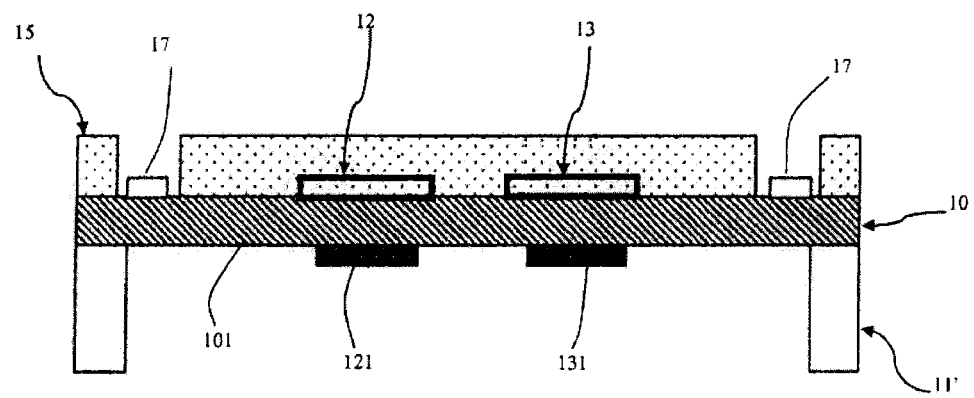

FIG. 5 illustrates another step, in which elements making it possible to make the temperature of each thermometric element 12 and 13 uniform are produced on the second face 101 of the membrane 10. These elements 121, 131 will, hereinafter in the description, be called isothermal elements.

These isothermal elements are obtained by placing a mask onto the second face 101 then by depositing, notably by magnetron sputtering, a metallic layer.

Preferably, a layer of a bond material, for example of WTi, will be deposited before the layer of metal.

The mask makes it possible to produce the two isothermal elements 121, 131 facing the two thermometric elements 12 and 13.

The metal used is, preferably, gold. The thickness of the bond material is typically 0.01 μm and that of the layer of gold 0.5 μm. The product then obtained is illustrated in FIG. 5.

Thus, all the steps of manufacture of the constituent elements of the sensor are carried out while the membrane is fixed onto a ring made of ceramic.

Because of its thermal extension coefficient, this ring 11' remains rigid and is not deformed at high temperature. Consequently, the membrane 10 will not undergo tensile stress during the various steps which have just been described in light of FIGS. 3 to 5.

This would not be the case if the membrane 10 were directly fixed to the copper ring 11.

Figure 6:
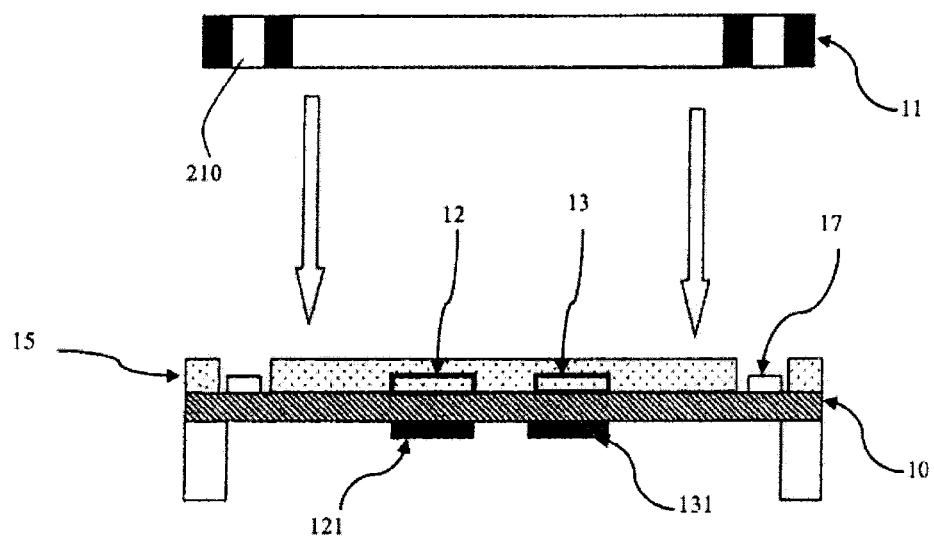

FIG. 6 illustrates the last step of the method, in which the copper ring 11 is bonded to the first face 100 of the membrane 10.

The ring 11' can then be eliminated.

On completion of this step, the thermometric cell 1, illustrated in FIGS. 1 and 2, is obtained.

Thus, the use, during the production method, of a ring made of ceramic, makes it possible to produce, with no stress, the thermometric elements 12 and 13. Furthermore, after the copper ring has been fixed, these elements will be protected, not only by the presence of the layer of resin 15, but also by the ring 11 itself.

The steps of production of a heating cell according to the invention are very similar to the steps of production of a thermometric cell which have just been described.

The description will therefore be simplified with regard to a heating cell, only the differences compared to the method described previously being highlighted.

Thus, on the first face 200 of the membrane 20 a layer of metal will be deposited, notably by magnetron sputtering.

The metal deposited is, preferably, an alloy of copper and nickel. With a proportion of 80% copper and 20% nickel, this alloy exhibits a fairly low temperature coefficient (a few hundred ppm per degree), which makes it a suitable material for heating.

This metal can be deposited directly onto the first face 200 of the membrane 20.

The active heating elements 22 and 23 are also obtained by a microphotolithography process.

However, the last step consisting in removing the part of the metallic layer which does not belong to the pattern is carried out by wet etching, that is to say an etching obtained by effecting a chemical attack in aqueous solution.

This alloy offers the advantage of having a resistivity which varies little as a function of temperature and its temperature coefficient is approximately $1.2 \cdot 10^{-4} K^{-1}$ from room temperature to 100° C. Consequently, a current of constant amplitude will be converted into almost constant calorific power, over wide temperature ranges.

In this exemplary embodiment, the heat capacity of the active heating elements 22 and 23 is 0.648 mJ/K.

When the cell 2 associated with the thermometric cell 1 does not include any heating element, its production is considerably simplified. In fact, it is obtained by fixing, on the first face 200 of the membrane, the support means 21.

It has thus been found that the heat capacity of the membrane, of the thermometric elements and of the heating elements is very low, which favors thermal diffusion and conductivity. Thus, it is possible to reduce the size of the samples while having a good resolution. Furthermore, in as much as the size of the samples is of the order of a microliter, the temperature ramps can be significant and range up to a hundred or so degrees per minute, without temperature gradients appearing.

Moreover, it should be noted that the sensitivity of the measurement obtained depends not only on the temperature coefficient of the thermometric elements, but also on their polarization (voltage or current). The sensitivity of the sensor can therefore be adapted to the physical chemistry of the sample, which gives it another advantage over the existing sensors.

As an example, the sensitivity of the measurement can be adapted by varying the polarization of the thermometers. For significant transitions to be detected, a lesser sensitivity will be chosen, whereas, for very fine thermal events to be detected, a greater sensitivity will be chosen by more strongly polarizating the thermometer. Of course, in this case, the power generated by the thermometer(s) will be greater and the temperature difference between the sensitive zones and the support will be greater. Thus, when the thermometers are mounted according to a Wheatstone bridge type scheme, a strong polarization of the Wheatstone bridge gives a high sensitivity in terms of volts per degree.

On the contrary, in the case of thermopiles (passive sensors), the sensitivity depends only on the number of couples used and the sensitivity cannot be selected once the sensor is produced.

Finally, the use of a ring made of ceramic material in the steps of microfabrication of the active heating elements makes it possible to protect the membrane 20 from any stress.

The sensor which has just been described can be used in a differential calorimeter, in conjunction with an oven in which the sensor is placed.

The tests carried out show that the sensor according to the invention makes it possible to obtain temperature ramp speeds of between 0.001 and 100° C./min, within a temperature range of between −20 and 170° C.

Moreover, the volume of the sample or of the reference is between 0.001 and 0.01 ml.

The tests also show that the sensor according to the invention exhibits a greater power sensitivity than the known calorimeters.

These tests consist in placing an identical sample between the two membranes of the sensor and between the two pairs of active elements, the temperature being 30° C.

Each heating cell is powered for 2 minutes, three different thermal power values being dissipated (0.01 mW, 0.3 mW and 1 mW), corresponding to dissipated energies of 1.2; 36 and 120 mJ.

The bridge output voltage is measured on the thermometric elements, and it is a differential measurement. The results obtained lead to a power sensitivity of the sensor of approximately 2.5 mV/mW, whereas the known sensors exhibit a sensitivity of the order of 100 µV/mW.

The reference signs inserted after the technical features appearing in the claims are solely to facilitate the understanding thereof and will not limit their scope.

The invention claimed is:

1. A differential calorimetric measurement sensor comprising:
   two cells, a thermometric cell and another cell, each cell comprising:
      a membrane made of a material with low thermal conductivity, with a first face and a second face, and support means for the membrane, made of a material exhibiting a high thermal diffusivity coefficient, in contact with the first face of the membrane;
   the thermometric cell comprising at least two active thermometric elements situated on the first face of the membrane and the two cells configured to be assembled such that the second faces of the membranes of the cells are facing one another, a sample and a reference used to perform the measurement configured to be placed between the two membranes and directly in contact with the second faces, and
   at least one of the cells comprising a closure means facing the first face of the membrane, a free space being formed between the closure means and the membrane for a gas, the closure means each including a piercing being in communication with the free space, and a height of the closure means being adapted in such a way as to create a thermal conduction of predetermined value via the gas between the membrane and the closure means.

2. The sensor as claimed in claim 1, in which the other cell is a heating cell, at least two active heating elements being situated on the first face of the membrane of the other cell, such that each of the active heating elements is substantially aligned with one of the active thermometric elements of the thermometric cell, when the two cells are assembled together, a sample and a reference used to perform the measurement then configured to be placed between two active elements of each of the two cells.

3. The sensor as claimed in claim 1, in which the second face of the membrane of at least one cell comprises, facing the at least two active elements, a layer made of a material exhibiting a high thermal conductivity.

4. The sensor as claimed in claim 1, in which the support means is situated at a periphery of the membrane.

5. The sensor as claimed in claim 1, in which the active elements of each cell are coated in a layer of electrically insulating material.

6. A differential calorimeter comprising:
   a measurement sensor as claimed in claim 1;
   an oven provided in which the sensor is arranged; and
   a cooling means, said cooling means consisting of the gas, which is in fluid communication with the free space for obtaining thermal conduction between an external environment and the sample and the reference.

7. A method for manufacturing a measurement sensor as claimed in claim 1, producing two cells, a thermometric cell and another cell, the thermometric cell comprising a membrane made of a material with low thermal conductivity, the method comprising:
   ($a_1$) producing at least two active elements simultaneously on a first face of the membrane;
   ($a_2$) fixing support means exhibiting a high thermal diffusivity coefficient onto the first face of the membrane;
   the other cell being obtained by performing the ($a_2$) and the cells configured to be assembled together, such that the second faces of the respective membranes of the cells are facing one another.

8. The method as claimed in claim 7, in which, prior to ($a_1$), performing ($a_0$) in which the membrane is fixed onto a ring made of ceramic material, the ring being in contact with the second face of the membrane, the method carrying out ($a_2$) after the ($a_1$), then performing ($a_3$) in which the ring is removed.

9. The method as claimed in claim 8, in which the other cell is a heating cell which is obtained by implementing the ($a_1$) and ($a_2$), at least two active heating elements being produced during the ($a_1$).

10. The method as claimed in claim 7, further comprising a complementary operation depositing, after the ($a_1$), a layer of electrically insulating resin, so as to coat the active elements of at least one of the two cells.

11. The method as claimed in claim 7, further comprising a complementary operation, after the ($a_1$), of depositing, on the second face of a membrane of at least one of the two cells, and facing a corresponding active element, a layer exhibiting a high thermal conductivity.

12. The method as claimed in claim 7, in which, for production of the thermometric cell, the ($a_1$) comprises:
   ($b_1$) deposition of a layer of metal;
   ($b_2$) a lithography; and
   ($b_3$) an ionic etching.

13. The method as claimed in claim 7, in which, for the production of a heating cell, the ($a_1$) comprises:
   ($b'_1$) deposition of a layer of metal;
   ($b'_2$) a lithography; and
   ($b'_3$) a wet etching.

14. The method as claimed in claim 8, in which the other cell is a heating cell which is obtained by further implementing the ($a_0$) and ($a_3$).

* * * * *